Figure 1:
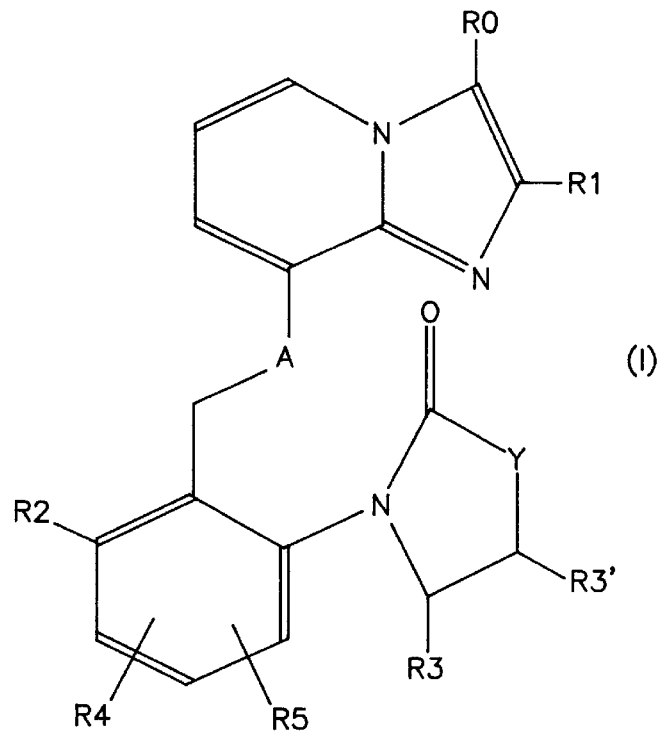

United States Patent [19]
Grundler et al.

[11] Patent Number: 6,124,313
[45] Date of Patent: Sep. 26, 2000

[54] IMIDAZOPYRIDINE AZOLIDINONES

[75] Inventors: Gerhard Grundler; Jörg Senn-Bilfinger; Ulrich Thibaut; Georg Rainer, all of Constance, Germany

[73] Assignee: Byk Gulden Lomberg Chemische Fabrik GmbH, Constance, Germany

[21] Appl. No.: 08/776,390

[22] PCT Filed: Jul. 26, 1995

[86] PCT No.: PCT/EP95/02954

§ 371 Date: Jan. 28, 1997

§ 102(e) Date: Jan. 28, 1997

[87] PCT Pub. No.: WO96/03405

PCT Pub. Date: Feb. 8, 1996

[30] Foreign Application Priority Data

Jul. 28, 1994 [CH] Switzerland ............ 2391/94

[51] Int. Cl.[7] .......... C07D 471/04; C07D 401/10; C07D 401/12; A61K 31/415
[52] U.S. Cl. .......... 514/300; 546/121
[58] Field of Search ............ 546/121; 514/300

[56] References Cited

U.S. PATENT DOCUMENTS

| 4,409,226 | 10/1983 | Bristol | 546/121 |
|---|---|---|---|
| 4,450,164 | 5/1984 | Bristol | 546/121 |
| 4,725,601 | 2/1988 | Ueda | 514/300 |
| 4,831,041 | 5/1989 | Shiokawa | 514/300 |
| 4,920,129 | 4/1990 | Shiokawa | 514/300 |

FOREIGN PATENT DOCUMENTS

| 0 033 094 | 8/1981 | European Pat. Off. . |
| 0 228 006 | 7/1987 | European Pat. Off. . |
| 0 266 890 | 5/1988 | European Pat. Off. . |
| 0 596 406 | 5/1994 | European Pat. Off. . |
| 94/18199 | 8/1994 | WIPO . |
| 95/10518 | 4/1995 | WIPO . |

OTHER PUBLICATIONS

*Chemical Abstracts*, vol. 115, No. 21, abstract No. 232239f, 1991 (Fujisawa JP–A–02 270 873).

*Primary Examiner*—John M. Ford
*Attorney, Agent, or Firm*—Jacobson, Price, Holman & Stern, PLLC

[57] ABSTRACT

Imidazopyridine-azolidinones are useful for treating or preventing amenable gastro-intestinal ailments.

16 Claims, 2 Drawing Sheets

Formulation sheet 1

Formulation sheet I

Formulation sheet II (III)

(IV)

IMIDAZOPYRIDINE AZOLIDINONES

This is a 371 of PCT/EP95/02954, filed 26 July 1995.

FIELD OF APPLICATION OF THE INVENTION

The invention relates to novel imidazopyridine azolidinones which are intended to be used in the pharmaceutical industry as active compounds for the production of medicaments.

KNOWN TECHNICAL BACKGROUND

European Patent Application EP-A-0 033 094 (partially equivalent to U.S. Pat. No. 4,450,164) describes imidazo[1,2-a]pyridines which in the 8-position carry an aryl substituent which is preferably a phenyl, thienyl, pyridyl, or chlorine-, fluorine-, methyl-, tert-butyl-, trifluoromethyl-, methoxy- or cyano-substituted phenyl radical. As aryl radicals of particular interest, EP-A-0 033 094 mentions the radicals phenyl, o- or p-fluorophenyl, p-chlorophenyl and 2,4,6-trimethylphenyl, of which the radicals phenyl, o- or p-fluorophenyl and 2,4,6-trimethylphenyl are particularly preferred.—European Patent Applications EP-A-0 204 285 (equivalent to U.S. Pat. No. 4,725,601), EP-A-0 228 006, EP-A-0 268 989 (equivalent to U.S. Pat. No. 4,831,041) and EP-A-0 308 917 (equivalent to U.S. Pat. No. 4,920,129) describe imidazo[1,2-a]pyridines which in the 3-position carry an unsaturated aliphatic radical, in particular a (substituted) alkynyl radical.—European Patent Application EP-A-0 266 890 describes imidazo[1,2-a]pyridines which are substituted in the 8-position by an alkenyl, alkyl or cycloalkylalkyl radical.

DESCRIPTION OF THE INVENTION

It has now been found that the compounds described in greater detail below, which in particular differ from the compounds of the prior art by the substitution in the 8-position, have surprising and particularly advantageous properties.

The invention relates to compounds of the formula I (see attached formula sheet I), in which R0 is 1–4C-alkyl, hydroxymethyl, halogen or thiocyanate,
R1 is 1–4C-alkyl,
R2 is hydrogen, 1–4C-alkyl, 1–4C-alkoxy, halogen or trifloromethyl,
R3 is hydrogen or 1–4C-alkyl,
R3' is hydrogen, 1–4C-alkyl or substituted 1–4C-alkyl having one or two identical or different substituents selected from the group consisting of halogen, 1–4C-alkoxy and 1–4C-alkoxy-1–4C-alkoxy,
R4 is hydrogen, 1–4C-alkyl, 1–4C-alkoxy, halogen or trifluoromethyl,
R5 is hydrogen, 1–4C-alkyl, 1–4C-alkoxy or halogen,
A is O (oxygen) or NH and
Y is O (oxygen) or $CH_2$,
and their salts.

1–4C-Alkyl is a straight-chain or branched alkyl radical having 1 to 4 carbon atoms. Examples which may be mentioned are the butyl, isobutyl, sec-butyl, tert-butyl, propyl, isopropyl, ethyl and, in particular, the methyl radical.

Halogen within the meaning of the invention is bromine, fluorine and in particular chlorine.

1–4C-Alkoxy is an oxygen atom to which one of the abovementioned 1–4C-alkyl radicals is bonded. Examples which may be mentioned are the methoxy and the ethoxy radical.

1–4C-Alkoxy-1–4C-alkoxy is one of the abovementioned 1–4C-alkoxy radicals which is substituted by a further 1–4C-alkoxy radical. An example which may be mentioned is the methoxyethoxy radical.

Suitable salts of compounds of the formula I are preferably all acid addition salts. Particular mention may be made of the pharmacologically tolerable salts of the inorganic and organic acids customarily used in pharmacy. Pharmacologically nontolerable salts which can initially be obtained as process products, for example, in the preparation of the compounds according to the invention on the industrial scale are converted into pharmacologically tolerable salts by the processes known to the person skilled in the art. Those suitable are water-soluble and water-insoluble acid addition salts with acids, such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

Compounds to be emphasized are those of the FIG. 1 (compounds I), in which

R0 is 1–4C-alkyl, hydroxymethyl or halogen,
R1 is 1–4C-alkyl,
R2 is 1–4C-alkyl or halogen,
R3 is hydrogen or 1–4C-alkyl,
R3' is hydrogen, 1–4C-alkyl or substituted 1–4C-alkyl having a substituent selected from the group consisting of halogen, 1–4C-alkoxy and 1–4C-alkoxy-1–4C-alkoxy,
R4 is hydrogen,
R5 is hydrogen,
A is O (oxygen) or NH and
Y is O (oxygen) or $CH_2$,
and their salts.

Compounds to be particularly emphasized are those compounds I, in which

R0 is methyl, hydroxymethyl, chlorine or fluorine,
R1 is methyl,
R2 is 1–4C-alkyl,
R3 is hydrogen or 1–4C-alkyl,
R3' is hydrogen, 1–4C-alkyl or substituted 1–4C-alkyl having a substituent selected from the group consisting of 1–4C-alkoxy and 1–4C-alkoxy-1–4C-alkoxy,
R4 is hydrogen,
R4 is hydrogen,
A is O (oxygen) or NH and
Y is O (oxygen) or $CH_2$,
and their salts.

Preferred compounds I are in which

R0 is methyl, hydroxymethyl or chlorine,
R1 is methyl,
R2 is 1–4C-alkyl,
R3 is hydrogen or 1–4C-alkyl,
R3' is hydrogen, 1–4C-alkyl, 1–4C-alkoxy-1–4C-alkyl or 1–4C-alkoxy-1–4C-alkoxy-1–4C-alkyl,
R4 is hydrogen,
R5 is hydrogen, A is O (oxygen) or NH
Y is O (oxygen) or $CH_2$,
and their salts.

Exemplary compounds according to the invention are listed in Table 1 which follows:

TABLE 1

Compounds I (see attached formula sheet) with R1 = $CH_3$, R4 = H, R5 = H and the following further substituent and symbol meanings:

| R0 | R2 | R3 | R3' | A | Y |
|---|---|---|---|---|---|
| F | $CH_3$ | H | H | NH | O |
| F | $CH_3$ | H | H | NH | $CH_2$ |
| F | $CH_3$ | H | H | O | O |
| F | $CH_3$ | H | H | O | $CH_2$ |
| Cl | $CH_3$ | H | H | O | O |
| Cl | $CH_3$ | H | H | NH | $CH_2$ |
| Cl | $CH_3$ | H | H | O | $CH_2$ |
| $CH_3$ | Cl | H | H | NH | O |
| $CH_2OH$ | Cl | H | H | NH | O |
| $CH_3$ | Cl | H | H | O | O |
| $CH_3$ | Cl | H | H | NH | $CH_2$ |
| Cl | Cl | H | H | NH | $CH_2$ |
| $CH_2OH$ | $CH_3$ | H | H | NH | $CH_2$ |
| $CH_3$ | $CH_3$ | H | $CH_2OCH_2CH_2OCH_3$ | NH | O |
| $CH_3$ | Cl | H | $CH_2OCH_3$ | NH | O | and the salts of the compounds mentioned in the table.

Compounds of I can each have a chiral center in the positions to which the substituents R3 and R3' are bonded. In the case of the chiral compounds, the invention therefore includes both the pure enantiomers and diastereomers and their mixtures in any mixing ratio, including the racemates.

Figure 2:
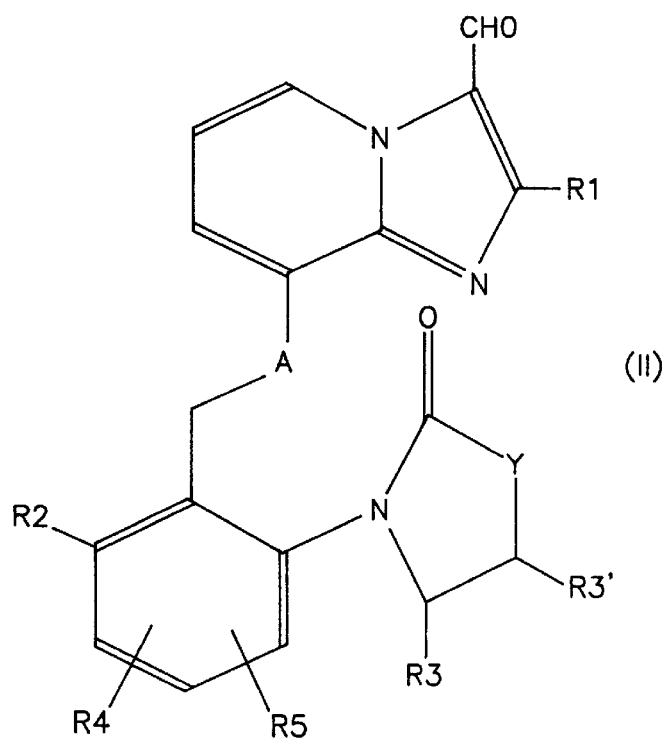
Figure 3:
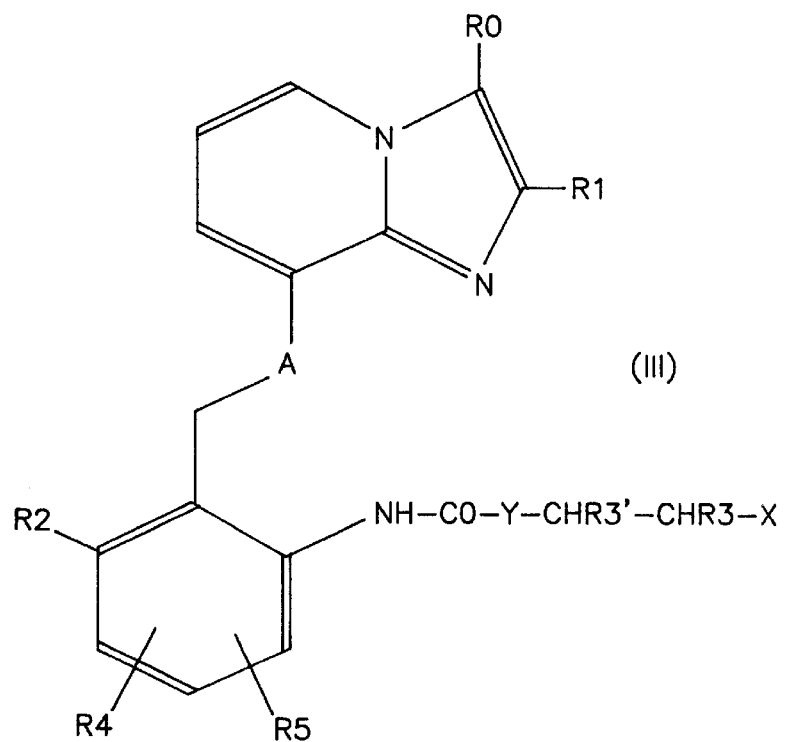

The invention further relates to a process for the preparation of I and their salts. The process comprises a) for the preparation of compounds I in which R0 is hydroxymethyl, reducing compounds FIG. 2 (compounds II) (see attached formula sheet I), in which R1, R2, R3, R3', R4, R5, A and Y have the meanings indicated above, or b) cyclizing compounds of FIG. 3 (compounds II) (see attached formula sheet II), in which R0, R1, R2, R3, R3', R4, R5, A and Y have the meanings indicated above and X is a suitable leaving group, with elimination of HX, and if desired then converting the compounds I obtained into their salts, or if desired then liberating the compounds I from salts of the compounds I obtained.

The reduction of the compounds II is performed in a manner customary per se to the person skilled in the art. It is carried out in inert solvents, e.g. lower aliphatic alcohols, e.g. using suitable hydrides, such as, for example, sodium borohydride, if desired with addition of water.

The cyclization of the compounds III is carried out in a manner familiar per se to the person skilled in the art, for example as described in the following examples, in inert solvents and in the presence of an acid-binding agent (proton acceptor). Proton acceptors which may be mentioned are, for example, alkali metal hydroxides, such as sodium or potassium hydroxide, or metal hydrides, such as sodium hydride. A suitable leaving group is, for example, a halogen atom (preferably chlorine or bromine) or a methane-sulfonyloxy group.

The person skilled in the art is familiar on the basis of his expert knowledge with the reaction conditions which are specifically necessary for carrying out the process.

The isolation and purification of the substances according to the invention is carried out in a manner known per se, for example, in such d way that the solvent is distilled off in vacuo and the residue obtained is recrystallized from a suitable solvent or subjected to one of the customary purification methods, such as, for example, column chromatography on suitable support material.

Acid addition salts are obtained by dissolving the free base in a suitable solvent, e.g. in water, in a chlorinated hydrocarbon, such as methylene chloride or chloroform, a lower aliphatic alcohol (ethanol, isopropanol), a ketone, such as acetone, or an ether, such as THF or diisopropyl ether, which contains the desired acid, or to which the desired acid is then added.

The salts are obtained by filtration, reprecipitation, precipitation with a nonsolvent for the addition salt or by evaporation of the solvent. Salts obtained can be converted by basification, e.g. with aqueous ammonia solution, into the free bases, which in turn can be converted into acid addition salts. In this manner, pharmacologically nontolerable acid addition salts can be converted into pharmacologically tolerable acid addition salts.

The starting compounds II are obtained by cyclization of those compounds III in which R0 has the meaning CHO.

Figure 4:
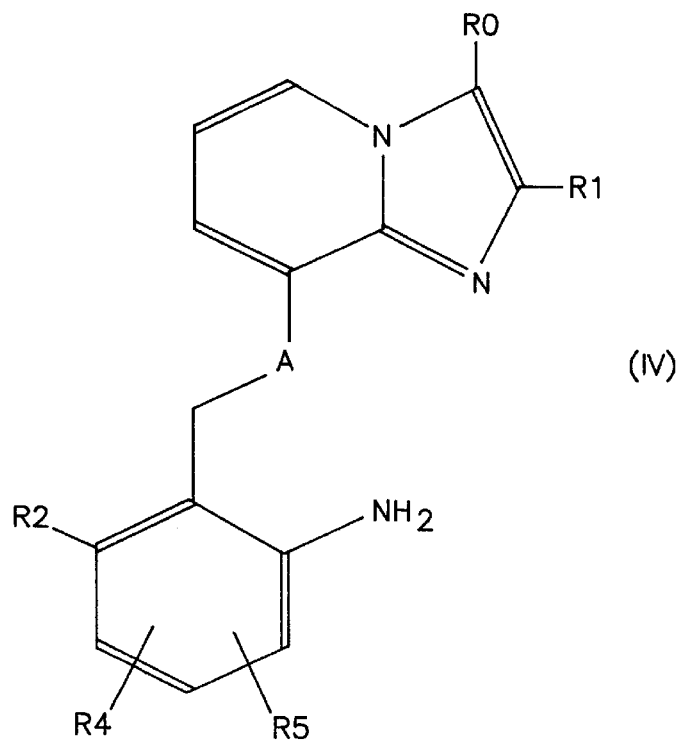

The compounds III are obtained, for example, by reaction of compounds of FIG. 4 (compounds IV) (see attached formula sheet II), in which R0, R1, R2, R4, R5 and A have the meanings indicated above, with compounds Hal-CO—Y—CHR3'—CHR3—X, in which R3, R3', Y and X have the meanings indicated above and Hal is a halogen atom (preferably chlorine or bromine).

The starting compounds IV are disclosed in EP-A-0 268 989 and EP-A-0 308 917 or they can be prepared in a manner analogous to that described there. For example, the starting compounds IV can be prepared in a manner known per se from the corresponding nitro compounds by reduction or by hydrolysis of suitable N-acyl derivatives.

The following examples serve to illustrate in greater detail the preparation of the compounds according to the invention. In particular, the examples also serve to describe by way of example the preparation of the compounds I and the preparation of selected starting compounds. Likewise, further compounds I and further starting compounds, whose preparation is not described explicitly, can be prepared in a manner which is analogous or in a manner which is familiar per se to the person skilled in the art using customary process techniques. The abbreviation RT stands for room temperature, h stands for hour(s), min stands for minute(s), m.p. for melting point, b.p. for boiling point and dec. for decomposition.

EXAMPLES

Final Products 1. 3-[2-(2,3-Dimethylimidazo[1,2-a]pyridin-8-yl] aminomethyl)-3-methylphenyl]oxazolidin-2-one a) 8-[2-(2-Chloroethoxycarbonylamino)-6-methylbenzylamino]-2,3-dimethylimidazo[1,2-a]pyridine 2-Chloroethyl chloroformate (12.4 g, 81 mmol) dissolved in dichloromethane (40 ml) is added dropwise at RT, during the course of about 30 min, to a solution of 8-(2-amino-6-methylbenzylamino)-2,3-dimethylimidazo[1,2-a]pyridine (19.65 g, 70 mmol) in anhydrous dichloromethane (600 ml). The mixture is then stirred at RT for 16 h and then extracted with sodium hydrogen carbonate (4×200 ml). After extraction of the aqueous phases with dichloromethane (200 ml), the combined organic extracts are washed with water (2×200 ml), dried over magnesium sulfate and concentrated. The crude product which remains (33.9 g) is used directly for the further reaction in Example 1b.

b) 3-[2-(2,3-Dimethylimidazo[1,2-a]pyridin-8-ylaminomethyl)-3-methylphenyl]oxazolidin-2-one Sodium hydride (3.15 g, 80% strength in paraffin) is added in portions with vigorous stirring in the course of about 30 min to a solution of the crude product from Example 1a (33.8 g) in anhydrous ethanol (800 ml). The mixture is then stirred for a further 30 min at RT, then water (200 ml) is added in portions and the ethanol is distilled off on a rotary evaporator. The precipitate is filtered off with suction, washed with water and dried in vacuo. The crude product is purified by chromatography on silica gel (eluent: toluene/dioxane=4:1). After concentration of the fractions of $R_f$=0.15 and crystallization from ethyl acetate/diisopropyl ether, the title compound (13.6 g, 63%) is isolated as a beige solid. M.p. 139–140° C.

c) Reaction of the title compound dissolved in acetone with methanesulfonic acid gives the methanesulfonate of the title compound of m.p. 232–235° C.

2. 3-[2-(3-Chloro-2-methylimidazo[1,2-a]pyridin-8-ylaminomethyl)-3-methylphenyl]oxazolidin-2-one a) 8-[2-(2-Chloroethoxycarbonylamino)-6-methylbenzylamino]-3-chloro-2-methylimidazo[1,2-a]pyridine According to the procedure indicated in Example 1a, 8-(2-amino-6-methylbenzylamino)-3-chloro-2-methylimidazo[1,2-a]pyridine (0.27 g) and 2-chloroethyl chloroformate (0.18 g) in dichloromethane (30 ml) give the title compound as a brown oil, which is used directly for further reaction in 2b.

b) 3-[2-(3-Chloro-2-methylimidazo[1,2-a]pyridin-8-ylaminomethyl)-3-methylphenyl]oxazolidin-2-one According to the procedure indicated in Example 1b, the crude product 2a (0.37 g) and sodium hydride (0.45 g, 80% strength in paraffin) in anhydrous ethanol (20 ml) give, after crystallization from ethyl acetate/petroleum ether, the title compound (70 mg, 21%) as a beige solid. M.p. 137–139° C.

3. 3-[2-(3-Hydroxymethyl-2-methylimidazo[1,2-a]pyridin-8-ylaminomethyl)-3-methylphenyl]oxazolidin-2-one a) 8-[2-(2-Chloroethoxycarbonylamino)-6-methylbenzylamino]-3-formyl-2-methylimidazo[1,2-a]pyridine According to the procedure indicated in Example 1a, 8-(2-amino-6-methylbenzylamino)-3-formyl-2-methylimidazo[1,2-a]pyridine (2.03 g) and 2-chloroethyl chloroformate (1.01 g) in dichloromethane (120 ml) give the title compound as a brown oil, which is used directly for further reaction in Example 3b.

b) 3-[2-(3-Formyl-2-methylimidazo[1,2-a]pyridin-8-ylaminomethyl)-3-methylphenyl]oxazolidin-2-one According to the procedure indicated in Example 1b, the crude product 3a (0.12 g) and sodium hydride (0.01 g, 80% strength in paraffin) in anhydrous ethanol (10 ml) give, after crystallization from ethyl acetate/diisopropyl ether, the title compound (80 mg, 73w) as a beige solid. M.p. 196–197° C.

c) 3-[2-(3-Hydroxymethyl-2-methylimidazo[1,2-a]pyridin-2-ylaminomethyl)-3-methylphenyl)oxazolidin-2-one A solution of 3-[2-(3-formyl-2-methylimidazo[1,2-a]pyridin-8-ylaminomethyl)-3-methylphenyl]oxazolidin-2-one (0.18 g, 0.49 mmol) and sodium borohydride (19 mg, 0.5 mmol) in anhydrous ethanol (20 ml) is stirred at RT for 30 min. Water (75 ml) is then added, the ethanol is distilled off on a rotary evaporator and the aqueous residue is extracted with ethyl acetate (3×50 ml). The organic extracts are washed with water (50 ml), dried over magnesium sulfate and concentrated. After crystallization from diisopropyl ether, the title compound (120 mg, 66%) is obtained as a beige solid. M.p. 152–157° C.

4. 3-[2-(3-Hydroxymethyl-2-methylimidazo[1,2-a]pyridin-8-yloxymethyl)-3-methylphenyl]oxazolidin-2-one a) 8-[2-(2-Chloroethoxycarbonylamino)-6-methylbenzyloxy]-3-formyl-2-methylimidazo[1,2-a]pyridine According to the procedure indicated in Example 1a, 8-(2-amino-6-methylbenzyloxy)-3-formyl-2-methylimidazo[1,2-a]pyridine (2.36 g) and 2-chloroethyl chloroformate (1.3 g) in dichloromethane (150 ml) give the title compound as a brown oil which is used directly for further reaction in 3b.

b) 3-[2-(3-Formyl-2-methylimidazo[1,2-a]pyridin-8-yloxymethyl)-3-methylphenyl]oxazolidin-2-one According to the procedure indicated in Example 1b, the crude product 4a (1.14 g) and sodium hydride (0.13 g, 80% strength in paraffin) in anhydrous ethanol (200 ml) give, after crystallization from ethyl acetate/diisopropyl ether, the title compound (0.7 g, 67%) as a beige solid. M.p. 242–244° C.

c) 3-[2-(3-Hydroxymethyl-2-methylimidazo[1,2-a]pyridin-8-yloxymethyl)-3-methylphenyl]oxazolidin-2-one A solution of 3-[2-(3-formyl-2-methylimidazo[1,2-a]pyridin-8-yloxymethyl)-3-methylphenyl]oxazolidin-2-one (1.39 g, 3.8 mmol) and sodium borohydride (0.19 g, 4.75 mmol) in anhydrous ethanol (125 ml) is stirred at RT for 1.5 h. Water (100 ml) is then added, the ethanol is distilled off on a rotary evaporator and the aqueous residue is stirred at 4° C. for 30 min. The precipitate is filtered off, washed with cold water and dried in vacuo. The title compound (1.28 g, 91%) is obtained as a beige solid. M.p. 190–193° C.

5. 5-Chloromethyl-3-[2-(2,3-dimethylimidazo[1,2-a]pyridin-8-ylaminomethyl)-3-methylphenyl]oxazolidin-2-one a) A mixture of 150 g (1.14 mol) of 1,3-dichloropropanol and 90.2 g (1.14 mol) of pyridine is added dropwise at 5–8° C. in the course of 2 h to 591 ml (1.14 mol) of a solution of phosgene in toluene (1.93 mol/l) and the mixture is stirred for a further 24 h at 20° C. It is aerated with $N_2$, pyridine hydrochloride is filtered off, the filtrate is washed with water and dried with magnesium sulfate, and after fractional distillation 102 g (47%) of 2-chloro-1-chloromethylethyl chloroformate are obtained. B.p. 140–145° C./18 mbar.

b) A solution of 2.0 g (7.13 mmol) of 8-(2-amino-6-methylbenzylamino)-2,3-dimethylimidazo[1,2-a]pyridine and 1.5 g (7.84 mmol) of the preceding compound in 80 ml of dichloromethane is stirred for 2 days at RT. The organic solution is washed with saturated sodium carbonate solution and water, dried with magnesium sulfate and concentrated in vacuo. 3.4 g of crude 8-(2-[(2-chloro-1-chloromethylethoxy)carbonylamino]-6-methylbenzylamino)-2,3-dimethylimidazo[1,2-a]pyridine are obtained as an oil, which is employed in the next stage.

c) A solution of 0.48 g of 85% potassium hydroxide in 4 ml of ethanol is added dropwise at 20° C. to a solution of the preceding compound in 30 ml of ethanol and the mixture is stirred for a further 5 h. It is concentrated in vacuo, the residue is treated with water, the mixture is extracted with dichloromethane and the magnesium sulfate-dried organic layer is concentrated in vacuo. The residue is treated with 5 ml of ethanol and cooled in an ice bath. 1.2 g of the title compound are obtained. M.p. 141–143° C.

6. 3-[2-(2,3-Dimethylimidazo[1,2-a]pyridin-8-ylaminomethyl)-3-methylphenyl]-5-methyloxazolidin-2-one hydrochloride a) Analogously to Example 5a, 2-chloro-1-propanol and phosgene give 2-chloro-1-methylethyl chloroformate. B.p. 55–56° C./17 mbar.

b) Analogously to Example 5b, 2.0 g (7.13 mmol) of 8-(2-amino-6-methylbenzylamino)-2,3-dimethylimidazo[1,2-a]pyridine and 1.23 g (7.85 mmol) of the previous compound are reacted and 3.1 g of crude 8-(2-[(2-chloro-1-methylethoxy)carbonylamino]-6-methylbenzylamino)-2,3-dimethylimidazo[1,2-a]pyridine are obtained as an amorphous mass.

b) A solution of 0.48 g of 85% KOH in 15 ml of ethanol is added dropwise at RT to 2.9 g of the previous compound in 15 ml of ethanol and the mixture is additionally stirred for 12 h. It is concentrated in vacuo, the residue is treated with water, the mixture is extracted with dichloromethane and the magnesium sulfate-dried organic layer is concentrated in vacuo. The residue is treated with 0.3 ml of concentrated hydrochloric acid and acetone and 1.5 g of the title compound are obtained. M.p. 274–275° C. (dec.).

7. 3-[2-(2,3-Dimethylimidazo[1,2-a]pyridin-8-ylaminomethyl)-3-methylphenyl]-4-methyloxazolidin-2-one a) Analogously to Example 5b, 2-chloropropyl chloroformate and 8-(2-amino-6-methylbenzylamino)-2,3-dimethylimidazo[1,2-a]pyridine give 8-[2-(2-chloropropoxycarbonylamino)-6-methylbenzylamino]-2,3-dimethylimidazo[1,2-a]pyridine.

b) The previous compound and a solution of potassium hydroxide in ethanol give, analogously to Example 5c, the title compound.

8. 3-[2-(2,3-Dimethylimidazo[1,2-a]pyridin-8-ylaminomethyl-3-methylphenyl]-5-methoxymethyloxazolidin-2-one a) Analogously to Example 5b, 8-[2-(1-chloromethyl-2-methoxyethoxycarbonylamino)-6-methylbenzylamino]-2,3-dimethylimidazo[1,2-a]pyridine is obtained from 1-chloromethyl-2-methoxyethyl chloroformate (Helv. Chim. Acta 44, 105, 1961) and 8-(2-amino-6-methylbenzylamino)-2,3-dimethylimidazo[1,2-a]pyridine.

b) The previous compound and a solution of potassium hydroxide in ethanol give, analogously to Example 5c, the title compound.

9. 1-[2-(2,3-Dimethylimidazo[1,2-a]pyridin-8-ylaminomethyl)-3-methylphenyl]pyrrolidin-2-one
a) 8-[2-(4-Chlorobutyrylamino)-6-methylbenzylamino]-2,3-dimethylimidazo[1,2-a]pyridine 0.88 ml (7.85 mmol) of 4-chlorobutyryl chloride is added dropwise at 0–5° C. with stirring to a solution of 2.2 g (7.85 mmol) of 8-(2-amino-6-methylbenzylamino)-2,3-dimethylimidazo[1,2-a]pyridine and 0.63 ml (7.85 mmol) of pyridine in 30 ml of dichloromethane and the mixture is stirred for a further 2 h at 0–20° C. It is treated with water and potassium hydrogen carbonate to pH 7, the mixture is extracted with shaking, and the organic layer is dried with magnesium sulfate and concentrated in vacuo. The residue is recrystallized from toluene and petroleum ether (50/70° C.). 2.6 g (86%) of the title compound are obtained. M.p. 138–140° C.

b) 1-[2-(2,3-Dimethylimidazo[1,2-a]pyridin-8-ylaminomethyl)-3-methylphenyl]pyrrolidin-2-one A solution of 0.41 g (6.25 mmol) of 85% KOH in 15 ml of ethanol is added dropwise at RT to a solution of 2.4 g (6.24 mmol) of the previous compound in 60 ml of ethanol and the mixture is stirred for a further 4 h. It is concentrated in vacuo to about 30 ml, the residue is diluted with water and the mixture is extracted several times by shaking with ethyl acetate. The organic layer is dried with magnesium sulfate and concentrated in vacuo, and the residue is crystallized using diisopropyl ether. 2.0 g (92%) of the title compound are obtained. M.p. 138–141° C.

10. 1-[2-(3-Chloro-2-methylimidazo[1,2-a]pyridin-8-ylaminomethyl)-3-methylphenyl]pyrrolidin-2-one
a) 8-[2-(4-Chlorobutyrylamino)-6-methylbenzylamino]-3-chloro-2-methylimidazo[1,2-a]pyridine According to the procedure indicated in Example 9a), the title compound is obtained by reaction of 8-(2-amino-6-methylbenzylamino)-3-chloro-2-methylimidazo-[1,2-a]pyridine and 4-chlorobutyryl chloride as a beige powder after crystallization from ethyl acetate/cyclohexane. Yield 66%; m.p. 127–130° C.

b) 1-[2-(3-Chloro-2-methylimidazo[1,2-a]pyridin-8-ylaminomethyl)-3-methylphenyl]pyrrolidin-2-one According to the procedure indicated in Example 9b), the title compound is obtained as a beige powder by reaction of the previous compound with potassium hydroxide in ethanol and subsequent crystallization from diisopropyl ether. Yield 77%; m.p. 265–267° C.

Starting Compounds
A1. 3-Chloro-2-methyl-8-pivaloylaminoimidazo[1,2-a]pyridine 5.0 g (18.6 mmol) of 2-methyl-8-pivaloylaminoimidazo[1,2-a]pyridine hydrochloride, prepared from 8-amino-2-methylimidazo[1,2-a]pyridine and pivaloyl chloride, m.p. 229–230° C., are dissolved in glacial acetic acid (20 ml) and chlorine gas is slowly passed in at 15° C. until the reaction has ended according to TLC checking (about 20 min). The solvent is then distilled off, the residue is taken up in ethyl acetate/water (in each case 30 ml), and the solution is rendered basic and extracted with saturated sodium hydrogen carbonate solution. The extract is then extracted again with ethyl acetate (3×30 ml). The combined organic extracts are washed with water (50 ml), dried over magnesium sulfate and concentrated. The residue is purified by chromatography on silica gel (eluent: toluene/dioxane=9:1). After concentration of the fractions of $R_f$=0.2, the title compound (4.1 g, 83%) is obtained as a colorless solid. M.p. 117–118° C.

A2. 8-Amino-3-chloroimidazo[1,2-a]pyridine

A suspension of 3-chloro-2-methyl-8-pivaloylaminoimidazo[1,2-a]pyridine (4.0 g, 15 mmol) in 60% strength sulfuric acid (25 ml) is stirred at 100° C. for 1 h. After cooling to RT, water (100 ml) is added and the mixture is adjusted to pH 10 using 10 N sodium hydroxide solution. It is then extracted with ethyl acetate (3×50 ml). The combined organic extracts are washed with water (50 ml), dried over magnesium sulfate and concentrated. The residue is taken up in boiling toluene, clarified with silica gel and crystallized. The title compound is isolated as a beige solid. Yield 1.9 g (70%), m.p. 126–127° C.

B2. 8-(6-Methyl-2-nitrobenzylamino)-2,3-dimethylimidazo [1,2-a] pyridine 15.0 g of sodium iodide and 31.0 g of sodium carbonate are added at RT to a solution of 8-amino-2,3-dimethylimidazo[1,2-a]pyridine (14.7 g) and 6-methyl-2-nitrobenzyl chloride (18.6 g) in 100 ml of acetone and the mixture is then heated at boiling under reflux for 6 h. After cooling the solution to RT and concentrating, the residue is dissolved in a mixture of 200 ml of ethyl acetate and 200 ml of water and the organic phase is separated off. After three further extractions with 100 ml of ethyl acetate each, the combined organic phases are dried over magnesium sulfate and then concentrated to 80 ml. 12.1 g of the title compound crystallize as a slightly yellow solid. The mother liquor is concentrated. Chromatographic purification of the residue on silica gel (eluent: toluene/dioxane=6:1) gives a further 14 g of the crystalline product. Recrystallization of both fractions from ethyl acetate gives 21.5 g (76%) of the title compound of m.p. 160–162° C.

B2. 8-(6-Methyl-2-nitrobenzyloxy)-2,3-dimethylimidazo-[1.2-al]pyridine

A suspension of 8-hydroxy-2,3-dimethylimidazo[1,2-a]pyridine (7.46 g, 46 mmol), 6-methyl-2-nitrobenzyl chloride (9.35 g, 50.4 mmol), sodium carbonate (11.24 g, 105 mmol) and sodium iodide (7.63 g, 50.4 mmol) in acetone (750 ml) is heated at reflux for 8 h. After cooling to RT, water (200 ml) is added and the acetone is distilled off on a rotary evaporator. The aqueous residue is then stirred at 4° C. for 30 min. The pale brown precipitate is then filtered off, washed with water and dried in vacuo. Further purification is carried out by chromatography on silica gel (eluent: toluene/dioxane=5:1). The fractions of $R_f$=0.2 are concentrated and recrystallized from ethyl acetate/cyclohexane. The title compound is isolated as a yellow solid. Yield 8.31 g (58%), m.p. 168–171° C.

B3. 3-Chloro-2-methyl-8-(6-methyl-2-nitrobenzylamino)imidazo[1,2-a] pyridine

Starting from 8-amino-3-chloroimidazo[1,2-a]pyridine (9.26 g), 6-methyl-2-nitrobenzyl chloride (10.5 g), sodium carbonate (13.7 g) and sodium iodide (8.55 g) in acetone (380 ml) according to the procedure indicated in Example B1 gives, after chromatography on silica gel (eluent: toluene/dioxane=20:1) and crystallization from ethyl acetate/cyclohexane, 10.6 g (63%) of the title compound of m.p. 142–144° C.

B4. 8-(2-tert-Butoxycarbonylamino-6-methylbenzylamino)-2,3-dimethylimidazo[1,2-a]pyridine Starting from 8-amino-2,3-dimethylimidazo[1,2-a]pyridine (4.8 g), 2-tert-butoxycarbonylamino-6-methylbenzyl chloride (9.2 g), sodium iodide (5.5 g) and sodium carbonate (8.0 g) in acetone (250 ml) analogously using the process of Example B1 gives, after chromatography on silica gel (eluent toluene/dioxane 20:1) and recrystallization from diisopropyl ether, 7.1 g (62%) of the title compound of m.p. 149–152° C.

B5. 8-(2-tert-Butoxycarbonylamino-6-methylbenzyloxy)-2,3-dimethylimidazo[1,2-a]pyridine Starting from 8-hydroxy-2,3-dimethylimidazo[1,2-a]pyridine (1.6 g), 2-tert-butoxycarbonylamino-6-methylbenzyl chloride (3.1 g), sodium iodide (1.8 g) and sodium carbonate (2.7 g) in acetone (350 ml) analogously using the process of Example B1 gives, after chromatography on silica gel (eluent toluene/dioxane 5:1) and recrystallization from cyclohexane, 3.0 g (78%) of the title compound of m.p. 128–131° C.

B6. 8-(2-tert-Butoxycarbonylamino-6-methylbenzylamino)-3-formyl-2-methylimidazo[1,2-a]pyridine Starting from 8-amino-3-formyl-2-methylimidazo[1,2-a]pyridine (4.0 g), 2-tert-butoxycarbonylamino-6-methylbenzyl chloride (7.0 g), sodium iodide (4.1 g) and sodium carbonate (6.1 g) in acetone (250 ml) analogously using the process of Example B1 gives, after chromatography on silica gel (eluent toluene/dioxane 9:1) and recrystallization from diisopropyl ether, 7.3 g (81%) of the title compound of m.p. 210–212° C.

B7. 8-(2-tert-Butoxycarbonylamino-6-methylbenzyloxy)-3-formyl-2-methylimidazo[1,2-a]pyridine Starting from 3-formyl-8-hydroxy-2-methylimidazo[1,2-a]pyridine (2.4 g), 2-tert-butoxycarbonylamino-6-methylbenzyl chloride (4.2 g), sodium iodide (2.5 g) and sodium carbonate (3.7 g) in acetone (400 ml) analogously using the process of Example B1 gives, after recrystallization from diisopropyl ether/ethyl acetate, 4.4 g (80%) of the title compound of m.p. 189–191° C.

C1. 8-(2-Amino-6-methylbenzylamino)-2,3-dimethylimidazo[1,2-a]pyridine

Method A

A solution of 8-(6-methyl-2-nitrobenzylamino)-2,3-dimethylimidazo[1,2-a]pyridine (61 g) in methanol (5.5 1) is hydrogenated at RT and under atmospheric pressure for 1.5 h in the presence of 15 g of palladium on active carbon (5%) as catalyst. After filtering off the catalyst and concentrating, the residue is dissolved in boiling ethyl acetate (2.7 l). After cooling to RT, 51 g (82%) of the title compound of m.p. 206–208° C. are isolated.

Method B 6.7 g of 8-(2-tert-butoxycarbonylamino-6-methylbenzylamino)-2,3-dimethylimidazo[1,2-a]pyridine are added at 25–30° C. in portions to a mixture of trifluoroacetic acid (30 ml) and anisole (3 ml). After stirring at RT for 30 minutes, the solution is poured into 100 ml of ice-water and then treated with 75 ml of 6N sodium hydroxide solution. The precipitate is filtered off and purified chromatographically on silica gel (solvent: toluene/dioxane=8:1). Recrystallization from ethyl acetate gives 3.1 g (62%) of the title compound of m.p. 206–208° C.

C2. 8-(2-Amino-6-methylbenzylamino)-3-formyl-2-methylimidazo[1,2-a]pyridine

Starting from 8-(2-tert-butoxycarbonylamino-6-methylbenzylamino)-3-formyl-2-methylimidazo[1,2-a]pyridine (3.6 g), trifluoroacetic acid (15 ml) and anisole (5 ml) according to the procedure described for Example C1 (Method B) gives, after chromatography on silica gel (eluent: toluene/dioxane=9:1) and crystallization from ethyl acetate/cyclohexane, 2.3 g (76%) of the title compound of m.p. 230–234° C.

C3. 8-(2-Amino-6-methylbenzyloxy)-3-formyl-2-methylimidazo[1,2-a]pyridine

Starting from 8-(2-tert-butoxycarbonylamino-6-methylbenzyloxy)-3-formyl-2-methylimidazo[1,2-a]pyridine (5.0 g) and trifluoroacetic acid (40 ml) analogously using the process of Example C1 (Method B) gives 3.57 g (96%) of the title compound of m.p. 144–150° C. (dec.).

C4. 8-(2-Amino-6-methylbenzylamino)-3-chloro-2-methylimidazo[1,2-a]pyridine hydrochloride A solution of 8-(2-nitro-6-methylbenzylamino)-3-chloro-2-methylimidazo[1,2-a]pyridine (2.0 g, 6 mmol) in methanol (175 ml) and dioxane (175 ml) is treated with platinum-on-carbon catalyst (5% strength) and hydrogenated at RT under atmospheric pressure for 2 h. After 2 h, 2N hydrochloric acid (5 ml) is added and the mixture is hydrogenated under the same conditions again for 1 h. The catalyst is then filtered off, the filtrate is adjusted to pH 8.5 using 2N sodium hydroxide solution and the solvent is distilled off on a rotary evaporator. The residue is dissolved in boiling ethyl acetate (400 ml). After cooling to RT, diisopropyl ether (250 ml) is added and, to complete crystallization, the mixture is stirred at 4° C. for 30 min. The precipitate is then filtered off with suction, washed with diisopropyl ether and dried in vacuo. The title compound (1.66 g, 92%) is isolated as a beige solid. M.p. 243–246° C.

Commercial Utility

The compounds I and their salts have useful pharmacological properties which make them commercially utilizable. In particular, they have a marked inhibition of gastric acid secretion and an excellent gastric and intestinal protective action in warm-blooded mammals. The compounds according to the invention are distinguished here by a high selectivity of action, a comparatively long duration of action, a good enteral activity, the absence of significant side effects and a large therapeutic breadth.

"Gastric and intestinal protection" in this connection is understood as meaning the prevention and treatment of gastrointestinal diseases, in particular gastrointestinal inflammatory diseases and lesions (such as, for example, gastric ulcer, duodenal ulcer, gastritis, hyperacidic or medicament-related functional gastropathy), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations. The compounds according to the invention in this case also have an intrinsic action against the microorganism *Helicobacter pylori*.

The compounds according to the invention surprisingly prove clearly superior to the compounds known from the prior art in their excellent properties in various models in which the antiulcerogenic and the antisecretory properties are determined. On account of these properties, the compounds I and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention further relates to medicaments which contain one or more compounds I and/or their pharmacologically tolerable salts.

The medicaments are prepared by processes known per se, which are familiar to the person skilled in the art. As medicaments, the pharmacologically active compounds according to the invention (=active compounds) are either employed as such, or preferably in combination with suitable pharmaceutical auxiliaries or excipients, in the form of tablets, coated tablets, capsules, suppositories, patches, (e.g. as TTS), emulsions, suspensions or solutions, the active compound content advantageously being between 0.1 and 95% and it being possible to achieve by the appropriate choice of the auxiliaries and excipients a pharmaceutical administration form exactly suited to the active compound and/or to the desired onset of action (e.g. a sustained-release form or an enteric form).

The person skilled in the art is familiar on the basis of his expert knowledge with the auxiliaries and excipients which are suitable for the desired pharmaceutical formulations. Beside solvents, gel-forming agents, suppository bases, tablet auxiliaries and other active compound excipients, for example, antioxidants, dispersants, emulsifiers, antifoams, flavor corrigents, preservatives, solubilizers, colorants or, in particular, permeation promoters and complexing agents (e.g. cyclodextrins) can be used.

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of several, preferably 1 to 4, individual doses to achieve the desired result. In the case of a parenteral treatment, similar or (in particular in the case of intravenous administration of the active compounds), as a rule, lower doses can be used. Any person skilled in the art can easily fix the optimum dose and manner of administration of the active compounds in each case on the basis of his expert knowledge.

If the compounds and/or salts according to the invention are to be employed for the treatment of the above-mentioned diseases, the pharmaceutical preparations can also contain one or more pharmacologically active constituents of other pharmaceutical groups, such as antacids, for example aluminum hydroxide, magnesium aluminate; tranquilizers, such as benzodiazepines, for example diazepam; spasmolytics, such as, for example, bietamiverine, camylofin, anticholinergics, such as, for example, oxyphencyclimine, phencarbamide; local anesthetics, such as, for example, tetracaine, procaine; and optionally also enzymes, vitamins or amino acids.

Emphasis is to be given in this connection in particular to the combination of the compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or furthermore with so-called peripheral anticholinergics (e.g. pirenzepine, telenzepine) and also with gastrin antagonists with the aim of potentiating the main action in an additive or superadditive sense and/or of eliminating or of lowering the side effects, or furthermore the combination with substances having antibacterial activity (such as, for example, cephalosporins, tetracyclines, nalidixic acid, penicillins or alternatively bismuth salts) for the control of *Helicobacter pylori*.

Pharmacology

The excellent gastric protective action and the gastric acid secretion-inhibiting action of the compounds according to the invention can be detected in investigations on animal experimental models. The compounds according to the invention investigated in the model mentioned below have been provided with numbers which correspond to the numbers of these compounds in the examples.

Testing the Secretion-inhibiting Action on the Perfused Rat Stomach

Table A which follows shows the effect of the compounds according to the invention after intravenous administration on the pentagastrin-stimulated acid secretion of the perfused rat stomach in vivo.

TABLE A

| No. | Dose ($\mu$mol/kg) i.v. | Inhibition of acid secretion (%) |
|---|---|---|
| 1b | 3 | 100 |
| 9b | 3 | 100 |

Methodology

After tracheotomy, the abdomen of anesthetized rats (CD rats, female, 200–250 g; 1.5 g/kg i.m. urethane) was opened by a median upper abdominal incision and a PVC catheter was fixed transorally in the esophagus and a further one via the pylorus in such a way that the tubing ends just projected into the gastric lumen. The catheter leading from the pylorus led outwards via a side opening in the right abdominal wall.

After thorough irrigation (about 50–100 ml), warm physiological NaCl solution at 37° C. was continuously passed through the stomach (0.5 ml/min, pH 6.8–6.9; Braun-Unita I). In the effluate in each case collected at an interval of 15 minutes, the pH (pH meter 632, glass electrode EA 147; φ=5 mm, Metrohm) and, by titration with a freshly prepared 0.01 N NaOH to pH 7 (Dosimat 665 Metrohm), the secreted HCl were determined.

The stimulation of gastric acid secretion was effected by continuous infusion of 1 μg/kg (=1.65 ml/h) of i.v. pentagastrin (left femoral vein) for about 30 min after the end of the operation (i.e. after determination of 2 initial fractions). The substances to be tested were administered intravenously in 1 ml/kg of liquid volume 60 min after beginning the pentagastrin continuous infusion.

The body temperature of the animals was kept at a constant 37.8–38° C. by infrared irradiation and heating pads (automatic, continuous regulation by means of a rectal temperature sensor).

The table indicates the dose which led to a maximum inhibition of the acid secretion by about 100%.

We claim:
1. A compound of formula I

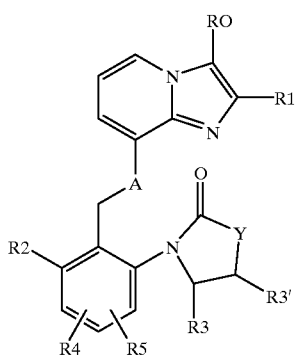

in which
R0 is 1–4C-alkyl, hydroxymethyl, halogen or thiocyanate,
R1 is 1–4C-alkyl,
R2 is hydrogen, 1–4C-alkyl, 1–4C-alkoxy, halogen or trifloromethyl,
R3 is hydrogen or 1–4C-alkyl,
R3' is hydrogen, 1–4C-alkyl or substituted 1–4C-alkyl having one or two identical or different substituents selected from the group consisting of halogen, 1–4C-alkoxy and 1–4C-alkoxy-1–4C-alkoxy,
R4 is hydrogen, 1–4C-alkyl, 1–4C-alkoxy, halogen or trifluoromethyl,
R5 is hydrogen, 1–4C-alkyl, 1–4C-alkoxy or halogen,
A is O (oxygen) or NH and
Y is O (oxygen) or CH$_2$,
or a salt thereof.

2. A compound of formula I as claimed in claim 1, in which
R0 is 1–4C-alkyl, hydroxymethyl or halogen,
R1 is 1–4C-alkyl,
R2 is 1–4C-alkyl or halogen,
R3 is hydrogen or 1–4C-alkyl,
R3' is hydrogen, 1–4C-alkyl or substituted 1–4C-alkyl having a substituent selected from the group consisting of halogen, 1–4C-alkoxy and 1–4C-alkoxy-1–4C-alkoxy,
R4 is hydrogen,
R5 is hydrogen,
A is O (oxygen) or NH and
Y is O (oxygen) or CH$_2$,
or a salt thereof.

3. A compound of formula I as claimed in claim 1, in which
R0 is methyl, hydroxymethyl, chlorine or fluorine,
R1 is methyl,
R2 is 1–4C-alkyl,
R3 is hydrogen or 1–4C-alkyl,
R3' is hydrogen, 1–4C-alkyl or substituted 1–4C-alkyl having a substituent selected from the group consisting of 1–4C-alkoxy and 1–4C-alkoxy-1–4C-alkoxy,
R4 is hydrogen,
R5 is hydrogen,
A is O (oxygen) or NH and
Y is O (oxygen) or CH$_2$,
or a salt thereof.

4. A compound of formula I as claimed in claim 1, in which
R0 is methyl, hydroxymethyl or chlorine,
R1 is methyl,
R2 is 1–4C-alkyl,
R3 is hydrogen or 1–4C-alkyl,
R3' is hydrogen, 1–4C-alkyl, 1–4C-alkoxy-1–4C-alkyl or 1–4C-alkoxy-1–4C-alkoxy-1–4C-alkyl,
R4 is hydrogen,
R5 is hydrogen,
A is O (oxygen) or NH
Y is O (oxygen) or CH$_2$,
or a salt thereof.

5. A compound of the formula I as claimed in claim 1, in which R0 is fluorine.

6. A medicament composition comprising a customary pharmaceutical auxiliary and/or excipient and an effective amount of a compound as claimed in claim 1 and/or a pharmacologically tolerable salt thereof.

7. A method for preventing or treating an amenable gastrointestinal disorder by administering an effective amount of active ingredient to a subject prone to or afflicted with such disorder, wherein the active ingredient is a compound as claimed in claim 1 or a pharmacologically tolerable salt thereof.

8. In a method which comprises administering an effective amount of a pharmaceutically-acceptable imidazopyridine to a subject prone to or afflicted with a gastrointestinal disorder which is prevented or alleviated by such treatment, the improvement wherein the imidazopyridine is a compound as claimed in claim 1 and/or a pharmaceutically tolerable salt thereof.

9. A method as claimed in claim 8 wherein Y is O (oxygen).

10. A method as claimed in claim 9 wherein A is NH.

11. A method as claimed in claim 8 wherein Y is CH$_2$.

12. A compound as claimed in claim 1 wherein Y is O (oxygen).

13. A compound as claimed in claim 12 wherein A is NH.

14. A compound as claimed in claim 1 wherein Y is CH$_2$.

15. The compound of claim 1 which is 3-[2-(2,3-dimethylimidazo[1,2-a]pyridin-8-yl]-aminomethyl)-3-methylphenyl]oxazolidin-2-one or a salt thereof.

16. The compound of claim 1 wherein R0=methyl, R1=methyl, R2=methyl, R3=hydrogen, R3'=hydrogen, R4=hydrogen, R5=hydrogen, A=NH and Y=O, or a salt thereof.

* * * * *